United States Patent [19]

Blount et al.

[11] Patent Number: 5,318,560
[45] Date of Patent: Jun. 7, 1994

[54] LASER DELIVERY SYSTEM

[75] Inventors: Gregory A. Blount, St. Charles, Mo.; Stanley Chang, Westchester, N.Y.; James C. Easley, St. Charles; Gregg D. Scheller, St. Louis, both of Mo.

[73] Assignee: Surgical Technologies, Inc., St. Louis, Mo.

[21] Appl. No.: 788,519

[22] Filed: Nov. 6, 1991

[51] Int. Cl.⁵ .............................................. A61N 5/02
[52] U.S. Cl. ......................................... 606/4; 606/6; 606/16; 604/902
[58] Field of Search ..................... 606/4, 6, 13, 14, 15, 606/16, 902

[56] References Cited

U.S. PATENT DOCUMENTS

| 3,964,484 | 6/1976 | Reynolds et al. | 604/902 |
| 4,825,865 | 5/1989 | Zelman | 606/6 |
| 5,112,328 | 5/1992 | Taboada et al. | 606/15 |
| 5,129,896 | 7/1992 | Hasson | 606/17 |

Primary Examiner—Stephen C. Pellegrino
Assistant Examiner—Sonya C. Harris
Attorney, Agent, or Firm—Polster, Lieder Woodruff & Lucchesi

[57] ABSTRACT

A laser delivery system for ophthalmic surgery and the like includes a handpiece, a laser connector, and an optical fiber for transmitting laser light from a laser source to an eye to be treated. The optical fiber extends through the handpiece tip. The tip also includes a fluid path from the distal end thereof to the interior of the handpiece body. The handpiece body has a fluid path in fluid communication with the fluid path of the tip, which fluid path extends to the exterior of the handpiece. The probe is inserted into the eye during surgery and may have multiple functions, reducing surgical complications. Fluid in the eye may flow through the tip and the handpiece body while laser light from the laser source is directed by the optical fiber into the eye. Structure is provided for refluxing material in the tip back into the eye as desired by the user. Alternatively, fluid may be delivered through the handpiece and tip to the surgical site if needed. A clamp is included to hold the optical fiber in place in an operating field if desired.

30 Claims, 2 Drawing Sheets

LASER DELIVERY SYSTEM

BACKGROUND OF THE INVENTION

The present invention relates to laser delivery systems and more particularly to such systems used in ophthalmic surgery and the like.

It is known that lasers may be used in ophthalmic surgery. Typically, the laser light is transmitted from a laser source (which is disposed at some distance from the patient) through an optical fiber cable (which can be eight feet or so in length) to the patient. The optical fiber cable terminates proximally in a laser connector (for connection to the laser source) and terminates distally in a handpiece which is manipulated by the surgeon.

Although such systems perform their desired function, they could be improved. For example, during ophthalmic surgery it is often necessary to remove blood and blood clots from the surface of the retina before laser treatment can be applied. Currently this is done by using a second probe (one in addition to the laser handpiece) which has a vacuum or suction capability. Given the small incision sizes used in eye surgery, it is often difficult to place the suction probe in the eye simultaneously with the laser probe and an illumination probe because of size limitations, and because the surgeon has only two hands. The laser handpiece must be removed from the eye during suction and replaced when laser treatment is required. This unnecessarily increases the complexity and duration of the medical procedure.

During such medical procedures, the suction probe occasionally draws in material (such as a portion of the retina) which must remain in the eye. Reflux of these materials from current suction probes is not always simple.

These medical procedures presently require at least two hands for operation of the laser handpiece and the suction probe, but both hands are generally not available since one hand is generally occupied with an illumination probe. As a result, the procedures presently require sequential replacement of laser handpiece and suction probe. Reflux of material from the suction probe can require even more hands and/or can significantly increase the complexity of the medical procedure.

Present laser delivery devices could also be improved in another way. Presently, the long optical cable is free to move throughout its length (except at the two ends). This can result in the cable contacting a non-sterile surface and thereby contaminating the sterile field.

SUMMARY OF THE INVENTION

Among the several objects and features of the present invention may be noted the provision of an improved laser delivery system which is especially suited for ophthalmic surgery or the like.

Another object is the provision of such a system which provides laser and suction capability in a single device.

A third object is the provision of such a system which provides suction capability precisely at the point where it is needed.

A fourth object is the provision of such a system which provides laser and suction capability in a device operable by one hand.

A fifth object is the provision of such a system which holds the optical cable thereof such that the possibility of contact with a non-sterile surface is reduced, without significantly reducing the ability of the surgeon using the system to move the handpiece freely.

A sixth object is the provision of such a system which is reliable, yet relatively simple to manufacture.

Other objects and features will be in part apparent and in part pointed out hereinafter.

Briefly, a laser delivery system of the present invention is especially suited for ophthalmic surgery and the like. The system includes a handpiece, a laser connector, and an optical cable. The handpiece has a handpiece body and a hollow tip of a size suitable for insertion into a human eye, which hollow tip extends distally from the handpiece body. The laser connector is suitably adapted for connection to a laser source. The optical fiber (terminating proximally in the laser connector and terminating distally in the handpiece) transmits laser light from a laser source to an eye to be treated. The optical fiber extends at least partially through the handpiece tip. The tip also includes a fluid path from the distal end thereof to the interior of the handpiece body. The handpiece body has a fluid path in fluid communication with the fluid path of the tip, which handpiece body fluid path extends to the exterior of the handpiece. With this construction fluid in the eye may flow through the tip and the handpiece body while laser light from the laser source is directed by the optical fiber into the eye.

In another aspect of the present invention, a laser delivery system for ophthalmic surgery and the like includes a handpiece having a handpiece body and a hollow tip of a size suitable for insertion into a human eye. The hollow tip extends distally from the handpiece body. A laser connector is included for connection to a laser source. An optical fiber terminating proximally in the laser connector and terminating distally in the handpiece is provided for transmitting laser light from a laser source to an eye to be treated. A clamp is included for removably securing an intermediate portion of the optical fiber in a fixed position with respect to an operating field.

BRIEF DESCRIPTION OF THE DRAWINGS

Similar reference characters indicate similar parts throughout the several views of the drawings.

DESCRIPTION OF THE PREFERRED EMBODIMENT

Turning to the drawings, a laser delivery system 11 of the present invention includes a handpiece 13, a laser connector 15, and an optical fiber cable 17. Handpiece 13 has a handpiece body made up of a handpiece proximal end portion 19, a handpiece distal end portion 21, and a reflux sleeve 23. A hollow metal tip 25 of a size suitable for insertion into a human eye extends distally from the handpiece body. Tip 25 is preferably a metal tube approximately one and three-quarters inches long which is suitably secured in the distal end of the handpiece body with approximately 1.38 inches of the tube exposed distally from the handpiece body. The outer diameter of the metal tube is, for example, approximately 0.0355 inch, and its inner diameter is approximately 0.025 inch. These dimensions are illustrative of those for a tip suitable for insertion in the human eye.

Laser connector 15 may be of any desired construction suitable for connection to a laser source (not shown). The construction shown is illustrative only.

Figure 1:
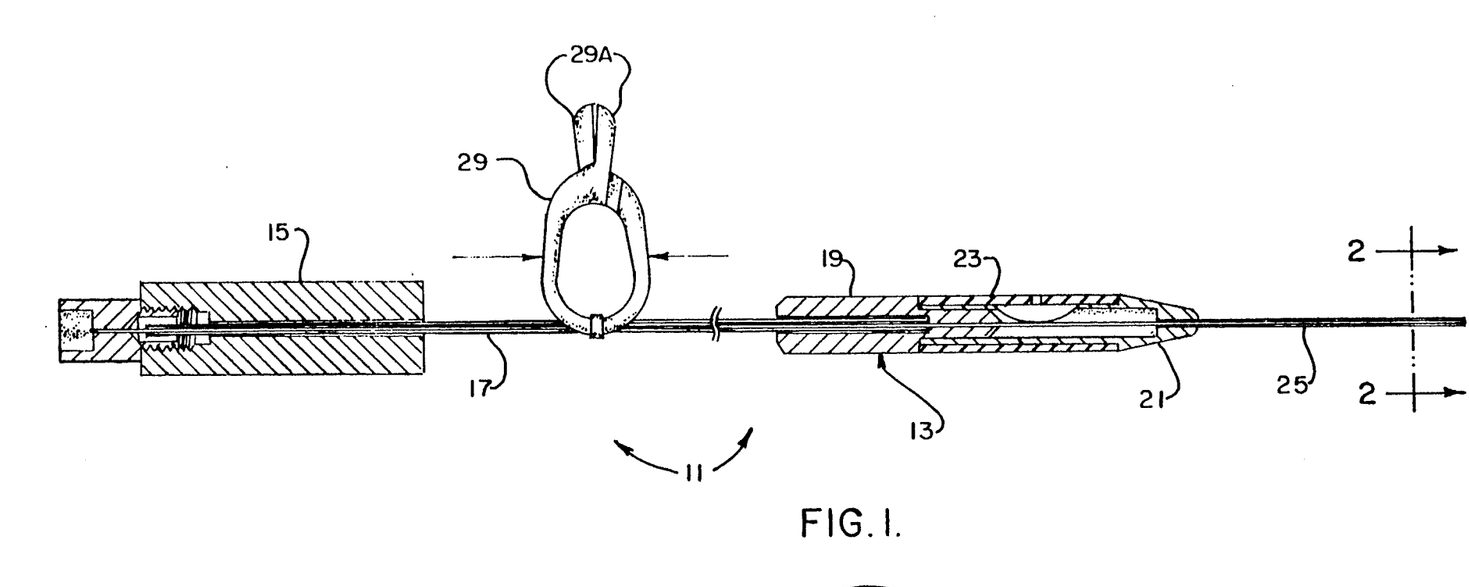
FIG. 1 is is a side view, with parts broken away for clarity, of the laser delivery system of the present invention.

As can be readily seen in FIG. 1, optical fiber cable 17 terminates proximally in laser connector 15 in such a manner that it is exposed to the laser light from the laser source. The optical cable extends for any desired length (such as eight feet or so) and terminates distally in the tip 25 of handpiece 13. Optical fiber cable 17 thereby forms an optical path for the laser light from the laser source to an eye being treated.

Also shown in FIG. 1 is a clamp 29 used to removably secure cable 17 to any appropriate structure to hold the cable in place without significantly restricting movement of the handpiece by the surgeon. For example, clamp 29 may be readily secured to a surgical drape (not shown) in the operative field by pressing both sides in the directions indicated by the arrows in FIG. 1. This pressure opens the jaws 29A of the clamp so that the jaws may be placed over a fold in the drape. Once the pressure is removed, the jaws close on the drape, thereby holding the optical cable fixed at that position in the surgical field. This prevents the optical cable from moving excessively during the medical procedure, which movement could otherwise result in contamination of the sterile field.

Figure 2:
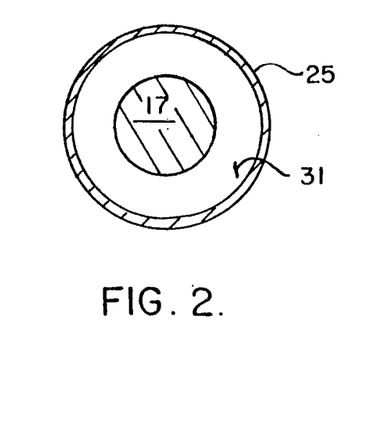
FIG. 2 is an enlarged sectional view taken along lines 2—2 of FIG. 1.

Turning to FIG. 2, there is shown on a greatly enlarged scale the relationship between optical cable 17 and tip 25. The portion of optical cable 17 which is disposed in tip 25 has an outer diameter of approximately 0.013", for example, while the inner diameter of the tip is approximately 0.025." This difference in diameter leaves a gap 31 disposed between the optical fiber and the tip. This gap runs the entire length of the tip and forms a fluid path from the distal end of tip 25 to the interior of the handpiece body.

Note that if the optical fiber were secured to tip 25 by adhesive (as has been done previously), the adhesive would tend to block off gap 31. To prevent this, the optical fiber is not secured directly to tip 25 at all. Instead it is suitably secured to proximal end portion 19 of the handpiece body. Note as well that, although the optical fiber 17 is shown centered in tip 25 in FIG. 2, the fiber can in fact be off-center in the tip without closing off gap 31.

The fluid path formed by gap 31 allows fluid and other material to be withdrawn through the gap. Significantly, the distal end of this fluid path is disposed immediately adjacent the spot where the laser light exits the tip, so that removal of fluid from the operative site takes place almost exactly where needed.

The fluid path formed by gap 31 is in fluid communication with a fluid path through handpiece 13. That latter fluid path is formed by a cavity 33 (FIG. 3) formed in handpiece distal end portion 21, which opens into a cavity 35 between handpiece distal end portion gi and reflux sleeve 23. Sleeve 23 has a port 37 formed therein above cavity 35, so that fluid in cavity 35 may flow out port 37 to the exterior of handpiece 13.

Figure 3:
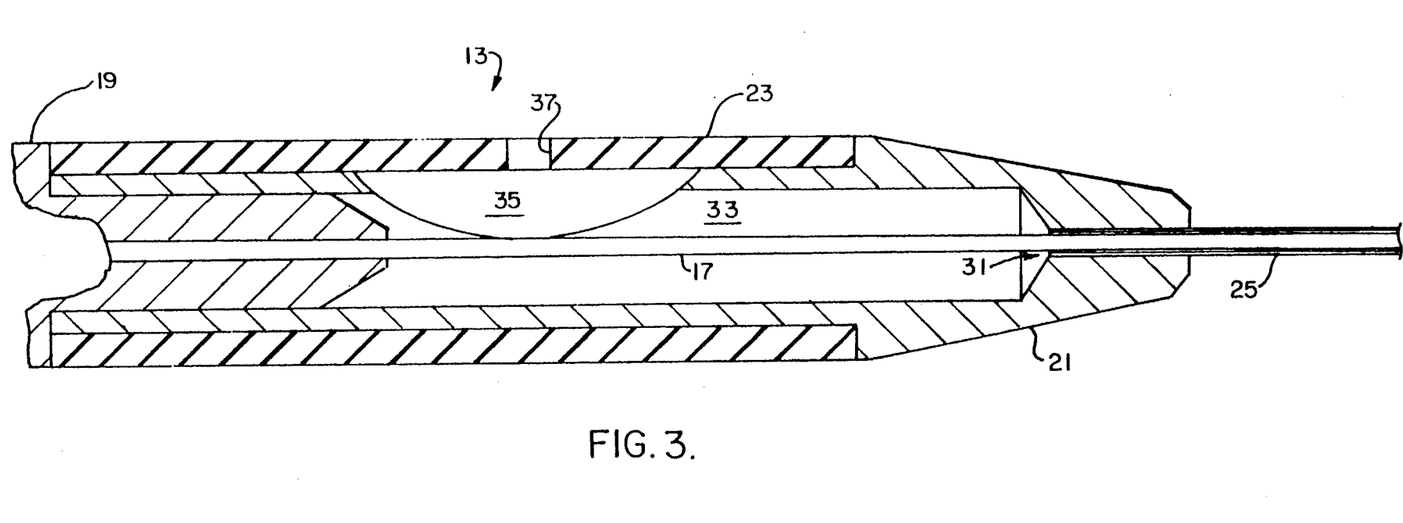
FIG. 3 is a sectional view, on an enlarged scale, of the distal end of the handpiece body of the laser delivery system of FIG. 1.

As is known, the interior of an eye being operated on may be placed under pressure with a suitable solution so as to maintain its sphericity during the procedure. This pressure causes fluid to flow through gap 31 in handpiece tip 25, through cavities 33 and 35, and out port 37. The surgeon can stop this flow simply by covering port 37 with a finger.

Note that with this construction, fluid in the eye may flow through the tip and the handpiece body even while laser light from the laser source is directed by the optical fiber into the eye. The surgeon, with one-handed control, can thus apply laser power to the surgical area while at the same time suction away fluid and other material from exactly the same area.

On occasion, distal tip 25 can suction in undesired material, such as a portion of the retina. With the present construction, this material can easily and rapidly be refluxed back into the eye, again with a one-handed operation. Reflux sleeve 23 is formed from a relatively soft, elastically deformable, resilient material such as 50 durometer silicone rubber. Note that port 37 is located directly over cavity 35 (which cavity is formed by cutting away the corresponding part of handpiece distal end portion 21). By pressing downwardly on sleeve 23 above cavity 35, the surgeon applies pressure on the fluid path from port 37 through the distal end of tip 25. This pressure forces any undesired material back out of the distal end of tip 25. Note that because port 37 is disposed directly above cavity 35, the mere act of pressing downwardly on the sleeve in this location automatically closes port 37. This ensures that the effect of the downward motion is to force fluid and any accompanying material distally out of tip 25.

It should be appreciated that the construction shown in FIG. 3 at best can expel a volume of material from the tip approximately equal to the volume of cavity 35. If it is desired to reflux a larger volume of material, the alternative construction of sleeve 23 shown in FIG. 4 may be used.

Figure 4:
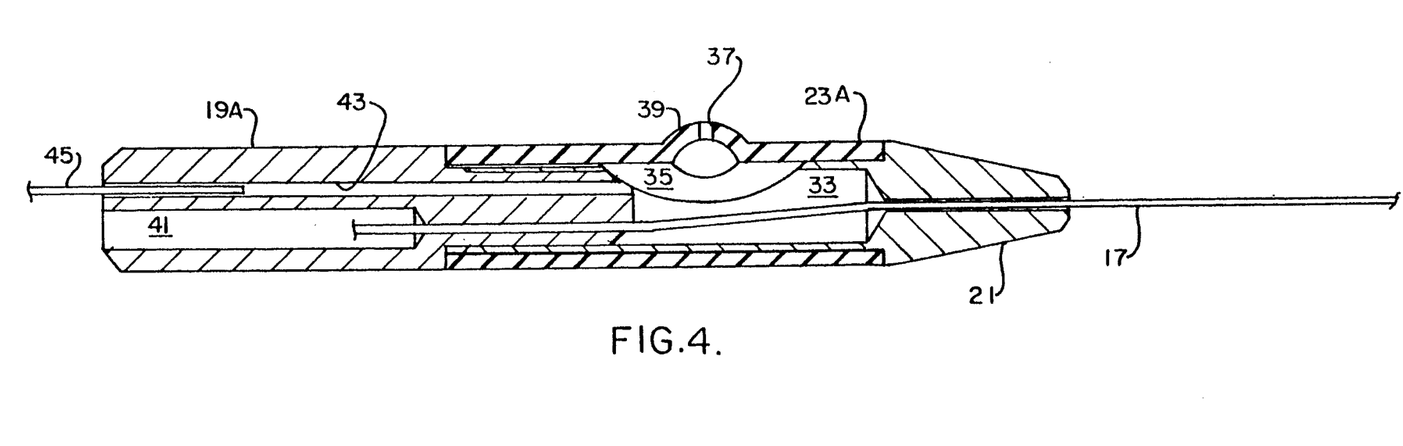
FIG. 4 is a sectional view, similar to FIG. 3, but on a somewhat smaller scale, of an alternative embodiment of the handpiece body of the present invention.

In FIG. 4, the reflux sleeve, labelled 23A, includes a hollow protrusion or bulb 39 in which is disposed port 37. The presence of bulb 39 increases the volume of material which can be expelled from tip 25, while at the same time providing a positive indication to the surgeon of the location of port 37. This positive indication is especially useful for locating the port while the surgeon is in the dark.

The handpiece of FIG. 4 also differs in having the capability of applying suction from a separate suction source (not shown) to the distal end of tip 25. Specifically, proximal section 19A of the handpiece shown in FIG. 4 has a first bore 41 through which passes optical fiber 17, and a second bore 43 in fluid communication with cavities 33 and 35. Bore 43 may be attached to any suitable suction source by means of a conventional tube 45 fixedly secured in bore 43.

Like the handpiece of FIG. 3, the one of FIG. 4 has the property that the application of pressure on the reflux sleeve above cavity 35 results in simultaneous closure of the fluid path through the handpiece.

As another alternative, the reflux means may include a tube (made of a suitable resilient material such as silicone or the like) which exits the handpiece at a suitable point at which it can be manually pressed or squeezed and then reenters the handpiece.

The apparatus of the present invention may also be used in other ways. For example, if there is a retinal detachment, one method of flattening the retina is to infuse an air bubble or silicone oil into the eye and then aspirate the subretinal fluid with a suction probe through a retinal tear or through a hole in the retina (retinotomy) made so the subretinal fluid can be aspirated. Conventionally, the suction probe is then removed and the laser probe introduced into the eye. The laser probe is used the seal the retinal tear when the retina is reattached. This prior art procedure requires replacing the suction probe with the laser probe. With the apparatus of the present invention, this replacement is unnecessary, thereby simplifying the procedure. In addition, sometimes fluid re-accumulates under the hole during the procedure, and with conventional equipment the laser cannot be immediately applied. With the apparatus of the present invention, the aspiration of the re-accumulated fluid may take place immediately, with no delay for switching probes.

The apparatus of the present invention is also especially suited for other methods or applications. If bleeding on the surface of the retina occurs during the operation, the bleeding vessel or tissue must be coagulated so that visibility of the tissues will not be obscured. Presently, the vacuuming needle or "flute needle" is used to remove the blood and then a separate diathermy probe (coagulating tip) is used to cauterize the tissue. Occasionally bleeding is so active that when instruments are exchanged, blood covers the bleeding tissue again. The apparatus of the present invention allows simultaneous aspiration of blood and the use of laser energy to coagulate surface bleeding, so visibility is not lost.

In addition, the structure of the apparatus of the present invention may be used to infuse small amounts of medication precisely to specific areas of the retina during surgery. For instance, if bleeding is encountered during surgery a small syringe containing thrombin (or other suitable blood clotting factor) may be applied locally over the bleeding site to clot the blood and prevent further bleeding. This is superior to the current system in which thrombin must be infused throughout the eye, exposing all the retinal tissue to thrombin, which may cause inflammation.

Moreover, the apparatus of the present invention may be used to deliver a small amount of laser activated tissue glue or adhesive to retinal tears or other target tissue using the same system. Then the laser is applied to activate the glue, forming the adhesive more precisely than is possible with present systems.

In view of the above it will be seen that the various objects and features of the above described invention are achieved and other advantageous results obtained. The description and drawings of the present invention contained herein are illustrative only and are not to be interpreted in a limiting sense.

What is claimed is:

1. A laser delivery system for ophthalmic surgery and the like comprising:
   a handpiece having a handpiece body by means of which the handpiece may be held and manipulated by a user and a hollow tip of a size suitable for insertion into a human eye, said hollow tip extending distally from the handpiece body;
   a laser connector for connection directly to a laser source;
   an optical fiber having a proximal end and a distal end, said optical fiber terminating at the proximal end in the laser connector and terminating at the distal end in the handpiece, said optical fiber forming a lenseless optical path for transmitting laser light from a laser source to an eye to be treated;
   said optical fiber extending through the handpiece body and at least partially through the handpiece tip, said tip having a proximal end and a distal end, said tip also including a fluid path from the distal end thereof to the interior of the handpiece body;
   said handpiece body having a fluid path in fluid communication with the fluid path of the tip, said handpiece body fluid path extending to the exterior of the handpiece, whereby fluid in the eye may flow through the tip and the handpiece body while laser light from the laser source is directed by the optical fiber into the eye;
   said handpiece body fluid path including a cavity inside the handpiece body and a port connecting said cavity to the exterior of the handpiece, said cavity being larger in cross-section than the fluid path in the handpiece tip.

2. A laser delivery system for ophthalmic surgery and the like comprising:
   a handpiece having a handpiece body and a hollow tip of a size suitable for insertion into a human eye, said hollow tip extending distally from the handpiece body;
   a laser connector for connection to a laser source;
   an optical fiber having a proximal end and a distal end, said optical fiber terminating at the proximal end in the laser connector and terminating at the distal end in the handpiece, said optical fiber forming a lenseless optical path for transmitting laser light from a laser source to an eye to be treated;
   said optical fiber extending at least partially through the handpiece tip, said tip having a proximal end and a distal end, said tip also including a fluid path from the distal end thereof to the interior of the handpiece body;
   said handpiece body having a fluid path in fluid communication with the fluid path of the tip, said handpiece body fluid path extending to the exterior of the handpiece, whereby fluid in the eye may flow through the tip and the handpiece body while laser light from the laser source is directed by the optical fiber into the eye; and
   means for refluxing material drawing into the fluid path from the eye back into the eye.

3. The laser delivery system as set forth in claim 2 wherein the handpiece body includes the refluxing means.

4. The laser delivery system as set forth in claim 2 wherein the refluxing means includes an elastically deformable member for exerting pressure on the fluid in the fluid path to push said material out of the tip back into the eye.

5. The laser delivery system as set forth in claim 2 wherein the refluxing means is manually operable.

6. The laser delivery system as set forth in claim 2 wherein the refluxing means includes a deformable sleeve disposed axially along the handpiece.

7. The laser delivery system as set forth in claim 6 wherein the deformable sleeve is disposed over a substantially rigid, tubular member, said tubular member having an orifice therethrough into which a portion of the sleeve may be pushed to exert pressure on the fluid in the fluid path.

8. The laser delivery system as set forth in claim 7 wherein the deformable sleeve has a port formed therein over the orifice, said port forming a portion of the fluid path to the exterior of the handpiece.

9. The laser delivery system as set forth in claim 6 wherein the deformable sleeve includes a hollow protrusion extending from the body of the sleeve, said hollow protrusion being in fluid communication with the interior of the sleeve and serving as a locator of the reflux means.

10. The laser delivery system as set forth in claim 2 wherein the refluxing means includes a deformable bulb extending outwardly from the handpiece.

11. The laser delivery system as set forth in claim 2 wherein the refluxing means includes means for simultaneously closing the fluid path through the handpiece upon operation of the refluxing means.

12. The laser delivery system as set forth in claim 2 wherein the refluxing means includes a resilient tube, a portion of which is disposed externally of the handpiece intermediate the ends of the handpiece, said exposed portion of the resilient tube being disposed such that the user may press upon the resilient tube during use of the handpiece.

13. A laser delivery system for ophthalmic surgery and the like comprising:
a handpiece having a handpiece body by means of which the handpiece may be held and manipulated by a user and a hollow tip of a size suitable for insertion into a human eye, said hollow tip extending distally from the handpiece body;
a laser connector for connection directly to a laser source;
an optical fiber having a proximal end and a distal end, said optical fiber terminating at the proximal end in the laser connector and terminating at the distal end in the handpiece, said optical fiber forming a lenseless optical path for transmitting laser light from a laser source to an eye to be treated;
said optical fiber extending through the handpiece body and at least partially through the handpiece tip, said tip having a proximal end and a distal end, said tip also including a fluid path from the distal end thereof to the interior of the handpiece body;
said handpiece body having a fluid path in fluid communication with the fluid path of the tip, said handpiece body fluid path extending to the exterior of the handpiece, whereby fluid in the eye may flow through the tip and the handpiece body while laser light from the laser source is directed by the optical fiber into the eye;
said handpiece body fluid path including a cavity inside the handpiece body, said cavity being larger in cross-section than the fluid path in the handpiece tip, a bore extending from the cavity to the exterior of the handpiece, and a tube for providing fluid communication between the bore and a suction source.

14. A laser delivery system for ophthalmic surgery and the like comprising:
a handpiece having a handpiece body by means of which the handpiece may be held and manipulated by a user and a hollow tip of a size suitable for insertion into a human eye, said hollow tip extending distally from the handpiece body;
a laser connector for connection directly to a laser source;
an optical fiber having a proximal end and a distal end, said optical fiber terminating at the proximal end in the laser connector and terminating at the distal end in the handpiece, said optical fiber forming a lenseless optical path for transmitting laser light from a laser source to an eye to be treated;
said optical fiber extending through the handpiece body and at least partially through the handpiece tip, said tip having a proximal end and a distal end, said tip also including a fluid path from the distal end thereof to the interior of the handpiece body;
said handpiece body having a fluid path in fluid communication with the fluid path of the tip, said handpiece body fluid path extending to the exterior of the handpiece, whereby fluid in the eye may flow through the tip and the handpiece body while laser light from the laser source is directed by the optical fiber into the eye;
further including means for removably securing an intermediate portion of the optical fiber in a fixed position with respect to an operating field, said intermediate portion of the optical fiber being disposed exteriorly of the handpiece.

15. A laser delivery system for ophthalmic surgery and the like comprising:
a handpiece having a handpiece body and a hollow tip of a size suitable for insertion into a human eye, said hollow tip extending distally from the handpiece body;
a laser connector for connection to a laser source;
an optical fiber having a proximal end and a distal end, said optical fiber terminating at the proximal end in the laser connector and terminating at the distal end in the handpiece, said optical fiber extending through the handpiece body and at least partially through the handpiece tip for transmitting laser light from a laser source to an eye to be treated; and
means for removably securing an intermediate portion of the optical fiber in a fixed position with respect to an operating field, said intermediate portion of the optical fiber being disposed exteriorly of the handpiece.

16. The laser delivery system as set forth in claim 15 wherein the removably securing means is a clamp.

17. The laser delivery system as set forth in claim 16 wherein the clamp is a one-piece plastic molded part.

18. The laser delivery system as set forth in claim 17 wherein said tip has a proximal end and a distal end, said tip also including a fluid path from the distal end thereof to the interior of the handpiece body, and wherein the handpiece body has a fluid path in fluid communication with the fluid path of the tip, said handpiece body fluid path extending to the exterior of the handpiece, whereby fluid in the eye may flow through the tip and the handpiece body while laser light from the laser source is directed by the optical fiber into the eye.

19. The laser delivery system as set forth in claim 15 further including means for refluxing material drawn into the fluid path from the eye back into the eye.

20. The laser delivery system as set forth in claim 19 wherein the handpiece body includes the refluxing means.

21. The laser delivery system as set forth in claim 19 wherein the refluxing means includes an elastically deformable member for exerting pressure on the fluid in the fluid path to push said material out of the tip back into the eye.

22. The laser delivery system as set forth in claim 19 wherein the refluxing means is manually operable.

23. The laser delivery system as set forth in claim 19 wherein the refluxing means includes a deformable sleeve disposed axially along the handpiece.

24. The laser delivery system as set forth in claim 23 wherein the deformable sleeve is disposed over a substantially rigid, tubular member, said tubular member having an orifice therethrough into which a portion of the sleeve may be pushed to exert pressure on the fluid in the fluid path.

25. The laser delivery system as set forth in claim 19 wherein the refluxing means includes a deformable bulb extending outwardly from the handpiece.

26. The laser delivery system as set forth in claim 19 wherein the refluxing means includes means for simultaneously closing the fluid path through the handpiece upon operation of the refluxing means.

27. The laser delivery system as set forth in claim 15 wherein the optical fiber is fixedly secured to the handpiece body and is otherwise loosely disposed in the handpiece tip.

28. A method of performing ophthalmic surgery comprising:
inserting the distal end of a probe into the interior of an eye;
aspirating material out of the interior of the eye through the probe;
applying laser energy through the probe into the interior of the eye, without replacing said probe;
infusing medication through the probe into the eye during surgery.

29. The method as set forth in claim 28 wherein the medication is a blood clotting factor, said step of infusing medication thereby including the step of clotting blood at the site where the medication is infused.

30. A method of performing ophthalmic surgery comprising:
inserting the distal end of a probe into the interior of an eye;
aspirating material out of the interior of the eye through the probe;
applying laser energy through the probe into the interior of the eye, without replacing said probe;
delivering an adhesive through the probe into the interior of the eye and activating the adhesive by the application of laser energy through the probe.

* * * * *

UNITED STATES PATENT AND TRADEMARK OFFICE
CERTIFICATE OF CORRECTION

PATENT NO. : 5,318,560
DATED : June 7, 1994
INVENTOR(S) : Gregory A. Blount, Stanley Chang, James C. Easley and Gregg D. Scheller It is certified that error appears in the above-identified patent and that said Letters Patent is hereby corrected as shown below:

Column 3, line 63, delete "gi" and insert --21--;

Column 10, line 6, after "said probe;" add --further including--.

Signed and Sealed this

Twentieth Day of September, 1994

Attest:

BRUCE LEHMAN

Attesting Officer  Commissioner of Patents and Trademarks

(12) EX PARTE REEXAMINATION CERTIFICATE (7572nd)
United States Patent
Blount et al.

(10) Number: US 5,318,560 C1
(45) Certificate Issued: Jun. 29, 2010

(54) LASER DELIVERY SYSTEM

(75) Inventors: Gregory A. Blount, St. Charles, MO (US); Stanley Chang, Westchester, NY (US); James C. Easley, St. Charles, MO (US); Gregg D. Scheller, St. Louis, MO (US)

(73) Assignee: Alcon Research, Ltd., Fort Worth, TX (US)

Reexamination Request:
No. 90/010,522, Jun. 10, 2009

Reexamination Certificate for:
Patent No.: 5,318,560
Issued: Jun. 7, 1994
Appl. No.: 07/788,519
Filed: Nov. 6, 1991

Certificate of Correction issued Sep. 20, 1994.

(51) Int. Cl.
*A61N 5/02* (2006.01)
*A61N 5/067* (2006.01)

(52) U.S. Cl. .................. 606/4; 606/6; 606/16; 604/902
(58) Field of Classification Search ........................ None
See application file for complete search history.

(56) References Cited

U.S. PATENT DOCUMENTS

| | | |
|---|---|---|
| 3,896,527 A | 7/1975 | Miller et al. |
| 4,180,074 A | 12/1979 | Murry et al. |
| 4,857,047 A | 8/1989 | Amoils |
| 5,098,444 A | 3/1992 | Feaster |
| 5,102,410 A | 4/1992 | Dressel |
| 5,129,882 A | 7/1992 | Weldon et al. |

OTHER PUBLICATIONS

R. Zivojnovic and G. J. Vijfvinkel; A Modified Flute Needle; American Journal of Ophthalmology; Oct. 1983, pp. 548–549; vol. 96, No. 4.

*Primary Examiner*—William C Doerrler (57) ABSTRACT

A laser delivery system for ophthalmic surgery and the like includes a handpiece, a laser connector, and an optical fiber for transmitting laser light from a laser source to an eye to be treated. The optical fiber extends through the handpiece tip. The tip also includes a fluid path from the distal end thereof to the interior of the handpiece body. The handpiece body has a fluid path in fluid communication with the fluid path of the tip, which fluid path extends to the exterior of the handpiece. The probe is inserted into the eye during surgery and may have multiple functions, reducing surgical complications. Fluid in the eye may flow through the tip and the handpiece body while laser light from the laser source is directed by the optical fiber into the eye. Structure is provided for refluxing material in the tip back into the eye as desired by the user. Alternatively, fluid may be delivered through the handpiece and tip to the surgical site if needed. A clamp is included to hold the optical fiber in place in an operating field if desired.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2-12 is confirmed.

Claims 1, 13, 14, 15, 28 and 30 are determined to be patentable as amended.

Claims 16-27 and 29, dependent on an amended claim, are determined to be patentable.

New claims 31-38 are added and determined to be patentable.

1. A laser delivery system for ophthalmic surgery and the like comprising:
   a handpiece having a handpiece body by means of which the handpiece may be held and manipulated by a user and a hollow tip of a size suitable for insertion into a human eye, said hollow tip extending distally from the handpiece body;
   a laser connector for connection directly to a laser source;
   an optical fiber having a proximal end and a distal end, said optical fiber terminating at the proximal end in the laser connector and terminating at the distal end in the handpiece, said optical fiber forming a lensless optical path for transmitting laser light from a laser source to an eye to be treated;
   said optical fiber extending through the handpiece body and at least partially through the handpiece tip, said tip having a proximal end and a distal end *and configured to permit the laser light to exit the tip for application to a surgical area*, said tip also including a fluid path from the distal end thereof to the interior of the handpiece body;
   said handpiece body having a fluid path in fluid communication with the fluid path of the tip, said handpiece body fluid path extending to the exterior of the handpiece, whereby fluid in the eye may flow through the tip and the handpiece body while laser light from the laser source is directed by the optical fiber into the eye;
   said handpiece body fluid path including a cavity inside the handpiece body and a port connecting said cavity to the exterior of the handpiece, said cavity being larger in cross-section than the fluid path in the handpiece tip.

13. A laser delivery system for ophthalmic surgery and the like comprising:
    a handpiece having a handpiece body by means of which the handpiece may be held and manipulated by a user and a hollow tip of a size suitable for insertion into a human eye, said hollow tip extending distally from the handpiece body;
    a laser connector for connection directly to a laser source;
    an optical fiber having a proximal end and a distal end, said optical fiber terminating at the proximal end in the laser connector and terminating at the distal end in the handpiece, said optical fiber forming a lensless optical path for transmitting laser light from a laser source to an eye to be treated;
    said optical fiber extending through the handpiece body and at least partially through the handpiece tip, said tip having a proximal end and a distal end *and configured such that the laser light exits the tip for application to a surgical area*, said tip also including a fluid path from the distal end thereof to the interior of the handpiece body;
    said handpiece body having a fluid path in fluid communication with the fluid path of the tip, said handpiece body fluid path extending to the exterior of the handpiece, whereby fluid in the eye may flow through the tip and the handpiece body while laser light from the laser source is directed by the optical fiber into the eye;
    said handpiece body fluid path including a cavity inside the handpiece body, said cavity being larger in cross-section than the fluid path in the handpiece tip, a bore extending from the cavity to the exterior of the handpiece, and a tube for providing fluid communication between the bore and a suction source.

14. A laser delivery system for ophthalmic surgery and the like comprising:
    a handiece having a handpiece body by means of which the handpiece may be held and manipulated by a user and a hollow tip of a size suitable for insertion into a human eye, said hollow tip extending distally from the handpiece body;
    a laser connector for connection cirectly to a laser source;
    an optical fiber having a proximal end and a distal end, said optical fiber terminating at the proximal end in the laser connector and terminating at the distal end in the handpiece, said optical fiber forming a lensless optical path for transmitting laser light from a laser source to an eye to be treated;
    said optical fiber extending through the handpiece body and at least partially through the handpiece tip, said tip having a proximal end and a distal end *and configured such that the laser light exits the tip for application to a surgical area*, said tip also including a fluid path from the distal end thereof to the interior of the handpiece body;
    said handpiece body having a fluid path in fluid communication with the fluid path of the tip, said handpiece body fluid path extending to the exterior of the handpiece, whereby fluid in the eye may flow through the tip and the handpiece body while laser light from the laser source is directed by the optical fiber into the eye;
    further including means for removably securing an intermediate portion of the optical fiber in a fixed position with respect to an operating field, said intermediate portion of the optical fiber being disposed exteriorly of the handpiece.

15. A laser delivery system for ophthalmic surgery and the like comprising:
    a handpiece having a handpiece body and a hollow tip of a size suitable for insertion into a human eye, said hollow tip extending distally from the handpiece body;

a laser connector for connection to a laser source;

an optical fiber having a proximal end and a distal end, said optical fiber terminating at the proximal end in the laser connector and terminating at the distal end in the handpiece, said optical fiber extending through the handpiece body and at least partially through the handpiece tip, [for transmitting] *said tip being configured to permit* laser light from a laser source *to exit the tip for transmission* to en eye to be treated; and means for removably securing an intermediate portion of the optical fiber in a fixed position with respect to an operating field, said intermediate portion of the optical fiber being disposed exteriorly of the handpiece.

28. A method of performing ophthalmic surgery comprising:

inserting the distal end of a probe into the interior of an eye;

aspirating material out of the interior of the eye through the probe;

applying laser energy through the probe into the interior of the eye *to a surgical area external to the probe*, without replacing said probe; further including infusing medication through the probe into the eye during surgery.

30. A method of performing ophthalmic surgery comprising:

inserting the distal end of a probe into the interior of an eye;

aspirating material out of the interior of the eye through the probe;

applying laser energy through the probe into the interior of the eye *such that the laser energy exits the probe for application to a surgical area*, without replacing said probe;

delivering an adhesive through the probe into the interior of the eye and activating the adhesive by the application of laser energy through the probe.

*31. The laser delivery system as set forth in claim 1 wherein the optical fiber is loosely disposed in the handpiece tip.*

*32. The laser delivery system as set forth in claim 2 wherein said hollow tip is configured to permit the laser light from the laser source to exit the tip for application to a surgical area.*

*33. The laser delivery system as set forth in claim 2 wherein said hollow tip is configured to permit the laser light from the laser source to exit the distal end of the tip for application to a surgical area.*

*34. The method as set forth in claim 28 wherein the steps of applying laser energy and aspirating material out of the interior of the eye are performed at the same time.*

*35. The laser delivery system set forth in claim 1 wherein said tip is configured to permit the laser light to exit the distal end of the tip for application to a surgical area.*

*36. The laser delivery system set forth in claim 13 wherein said tip is configured to permit the laser light to exit the distal end of the tip for application to a surgical area.*

*37. The laser delivery system set forth in claim 14 wherein said tip is configured to permit the laser light to exit the distal end of the tip for application to a surgical area.*

*38. The laser delivery system set forth in claim 15 wherein said tip is configured to permit laser light from a laser source to exit the distal end of the tip for transmission to an eye to be treated.*

* * * * *